United States Patent [19]
Watanabe

[11] Patent Number: 6,155,713
[45] Date of Patent: Dec. 5, 2000

[54] X-RAY DIAGNOSTIC APPARATUS HAVING AN X-RAY GENERATING PORTION AND AN X-RAY DETECTING PORTION INDEPENDENT OF EACH OTHER

[75] Inventor: Naoto Watanabe, Tochigi, Japan

[73] Assignee: Kabushiki Kaisha Toshiba, Kawasaki, Japan

[21] Appl. No.: 09/098,986

[22] Filed: Jun. 17, 1998

[30] Foreign Application Priority Data

Jun. 19, 1997 [JP] Japan ..................................... 9-162933

[51] Int. Cl.[7] ...................................................... A61B 6/00
[52] U.S. Cl. .......................................... 378/197; 378/98.8
[58] Field of Search .................................... 378/98.8, 189, 378/193, 195, 196, 197, 98.2, 167, 187, 177

[56] References Cited

U.S. PATENT DOCUMENTS

| | | | |
|---|---|---|---|
| 4,905,265 | 2/1990 | Cox et al. | 378/98.8 |
| 5,023,899 | 6/1991 | Ohison | 378/197 X |
| 5,434,418 | 7/1995 | Schick | 378/98.8 X |
| 5,572,566 | 11/1996 | Suzuki et al. | 378/98.8 |
| 5,636,259 | 6/1997 | Khutoryansky et al. | 378/197 |
| 5,661,309 | 8/1997 | Jeromin et al. | 378/98.8 X |
| 5,712,482 | 1/1998 | Gaiser et al. | 378/189 X |
| 5,715,292 | 2/1998 | Sayag et al. | 378/98.8 |
| 5,764,724 | 6/1998 | Ohison | 378/177 |
| 5,883,937 | 3/1999 | Schmitt | 378/98.8 X |
| 5,940,470 | 8/1999 | Palm-Plessmann et al. | 378/98.8 X |

Primary Examiner—David P. Porta
Attorney, Agent, or Firm—Oblon, Spivak, McClelland, Maier & Neustadt, P.C.

[57] ABSTRACT

An X-ray diagnostic apparatus has a first X-ray generating portion for imaging of over-table tube, a second X-ray generating portion for imaging of under-table tube, and an X-ray detecting portion having a compact and light solid state detector light attached to an elastic stay portion suspended from a ceiling to a floor. The solid state detector is supported by a central rotating arm for enabling central rotation about a central axis of the solid state detector, and an elastic offset rotating arm for enabling offset rotation dislocated from the central rotation. Therefore, by virtue of each rotation and the extension and contraction operation and further its compactness and lightness, the solid state detector can be accurately and rapidly set to various positionings in upward, downward, leftward, rightward and slanting positions, etc. with respect to a subject on a diagnostic table. An image of the subject is picked up by property using either of the X-ray generating portions in accordance with the positionings of the solid state detector.

26 Claims, 7 Drawing Sheets

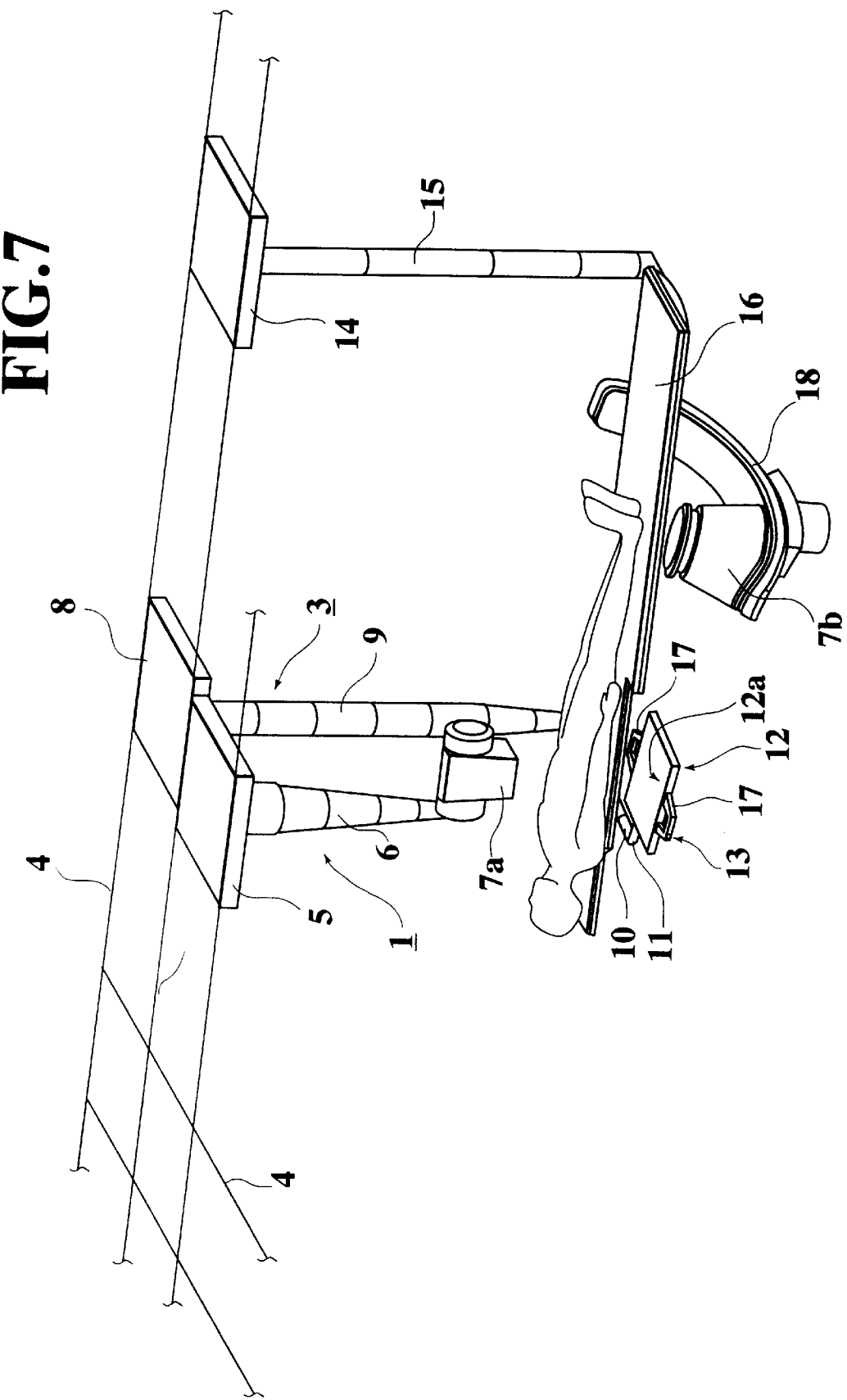

X-RAY DIAGNOSTIC APPARATUS HAVING AN X-RAY GENERATING PORTION AND AN X-RAY DETECTING PORTION INDEPENDENT OF EACH OTHER

BACKGROUND OF THE INVENTION

1. Field of the Invention

The present invention relates to an X-ray diagnostic apparatus, and particularly relates to an X-ray diagnostic apparatus in which an X-ray generating portion and an X-ray detecting portion are respectively independently arranged and can instantly cope with pickup images (fluoroscopy, radiography) in an over-table tube and an under-table tube and pickup images in various positionings.

2. Prior Art

In a holding device for a circulatory organ as a conventional X-ray diagnostic apparatus, an X-ray generating portion and an X-ray detecting portion are oppositely arranged in both end portions of an arm and are fixedly held. It is known that an arm shape is generally divided into a "C-type" having approximately a C-character shape and a "U-type" having approximately a U-character shape. However, in view of efficiency of three dimensional positioning, the C-type arm is arranged in many cases at present.

FIG.1 shows a perspective view of the holding device for a circulatory organ having this C-type arm.

As shown in FIG. 1, the holding device for a circulatory organ has a rail holding portion 100, a stay portion 101, a holder 102 and a C-type arm 103. The rail holding portion 100 movably holds the holding device for a circulatory organ along a rail attached to a ceiling. The stay portion 101 is rotatably suspended from this rail holding portion 100. The holder 102 is so held on a side of this stay portion 101 opposed to the rail holding portion 100 as to rotate about a main shaft. The C-type arm 103 is slidably held by this holder 102.

An X-ray generating portion 104 and an X-ray detecting portion 105 (an image intensifier, an optical system, a TV camera, etc.) are so arranged in both end portions of the C-type arm 103 as to be opposed to each other. The X-ray detecting portion 105 is so controlled by a moving mechanism 106 as to move upward and downward (toward the X-ray generating portion 104 and the opposite direction).

In such a holding device for a circulatory organ, the X-ray generating portion 104 and the X-ray detecting portion 105 arranged in both end portions of the C-type arm 103 are heavy in weight and large in size. Further, the C-type arm 103 has an asymmetrical shape. Accordingly, it is difficult to rotationally balance the C-type arm 103 in slide motion, main shaft rotation motion, etc. Therefore, positioning control of the C-type arm 103 is electrically performed by operating a dedicated handle, a joy stick, etc.

In contrast to this, separated holding devices generally called BC arms are known. In this separated holding devices, the X-ray generating portion and the X-ray detecting portion are separately held and are oppositely arranged. FIG.2A shows the constitution of the separated holding devices called the BC arms.

In FIG. 2A, the BC arms have a rail holding portion 120 and an elastic arm 121. The rail holding portion 120 can move the X-ray generating portion 124 along a rail attached to a ceiling. One end of the elastic arm 121 is so held by the rail holding portion 120 as to freely extend and contract. The X-ray generating portion 124 is arranged at the other end of the elastic arm 121. The BC arms also has a rail holding portion 122 and an elastic arm 123. The rail holding portion 122 can move the X-ray detecting portion 125 along the rail attached to the ceiling, independently to the movement of the X-ray generating portion 124. One end of the elastic arm 123 is so held by the rail holding portion 122 as to freely extend and contract. The X-ray detecting portion 125 is arranged at the other end of the elastic arm 123.

In such separated holding devices, only an oscillating movement, a horizontal movement and a vertical movement of the X-ray generating portion 124 (or the X-ray detecting portion 125) can be made. Accordingly, as shown in FIG. 3, the separated holding devices are mainly used for a lateral radiography as a lateral positioner of a biplane radiography.

FIG. 2B is a view showing a U-type arm as another positioner for biplane radiography.

In FIG. 2B, the U-type arm has a stay portion 110 and a U-type arm 111. The stay portion 110 is held by a rail holding portion for movably holding the U-type arm along a rail attached to a ceiling. The U-type arm 111 is so held on the side of the stay portion 110 opposed to the rail holding portion as to rotate about a main shaft 127. An X-ray generating portion 112 and an X-ray detecting portion 113 are oppositely arranged in both end portions of the U-type arm 111.

The separated holding devices shown in FIG. 2A have a low degree of freedom of positioning as mentioned above. Therefore, a device having an Ω-type arm having an Ω-character shape is used in many cases instead of the separated holding devices having the U-type arm.

In the conventional holding device for a circulatory organ, the X-ray detecting portion (I.I., an optical system, a TV camera, etc.) and the X-ray generating portion 104 as heavy objects are arranged in both end portions of the C-type arm 103 so that rotating inertia of the holding device is large. Further, the C-type arm 103 has an asymmetrical shape so that it is difficult to balance rotation of the C-type arm 103. Accordingly, positioning control of the holding device is electrically performed. However, a judgment about how to operate the holding device must be made to set desirable positioning. Further, skill is required to precisely perform an operation corresponding to each positioning and it is difficult to make a fine adjustment. Accordingly, it is difficult to accurately control the operation of the holding device in intended positioning.

It may be considered that this problem is solved by arranging a counterweight on the C-type arm 103, etc. to balance the rotation of the C-type arm 103, etc. so as to manually operate the holding device thereby making the fine adjustment of positioning by this manual operation. However, in this case, the rotating inertia of the holding device is increased so that there is also a fear that it is difficult to accurately set the desirable positioning.

It may be further considered that a solid state detector (a plane detector) formed by plural solid state image pickup elements is used as the X-ray detecting portion instead of an image intensifier (I.I) to facilitate the manual operation so as to make the holding device compact and light in weight. However, when this plane detector is used, the holding device is unbalanced in weight on the side of the X-ray generating portion 104 so that the moment of rotational inertia of the holding device is greatly increased in comparison with the present situation and there is also a fear that it is difficult to control the operation of the holding device.

The conventional separated holding devices can make only the oscillating movement, the horizontal movement and the vertical movement of the X-ray generating portion 124

(or the X-ray detecting portion 125). Therefore, the X-ray generating portion 124 (or the X-ray detecting portion) cannot be arranged under a subject. Accordingly, a problem exists in that an application range of the holding device is extremely limited (limited to an use as a lateral positioner of a biplane radiography).

SUMMARY OF THE INVENTION

The present invention has been achieved with such points of view. It therefore is an object of the present invention to provide an X-ray diagnostic apparatus capable of performing various positionings accurately and simply and accommodating to various ranges of application.

To achieve the above object, there is provided an X-ray diagnostic apparatus comprising: an X-ray generating portion for irradiating an X-ray to a subject; and a solid state detecting portion formed by plural solid state detecting elements for detecting the X-ray irradiated from the X-ray generating portion and movably provided independently of the X-ray generating portion.

Since such an X-ray diagnostic apparatus has the smaller and lighter solid state detecting portion light than an image intensifier, the X-ray diagnostic apparatus can easily hold the solid state detecting portion. Therefore, inertia of each movable section of the X-ray diagnostic apparatus can be reduced. Further, the X-ray generating portion and the solid state detecting portion can be independently moved. Therefore, various positionings of the X-ray generating portion and the solid state detecting portion can be accurately and rapidly set by compensating an influence caused by a weight of each movable portion. Accordingly, it is possible to accommodate to various ranges of application.

In a preferred embodiment of the present invention, the X-ray generating portion comprises at least one of an X-ray generating portion for an under-table tube capable of imaging in a style of under-table tube and an X-ray generating portion for an over-table tube capable of imaging in a style of over-table tube.

In a preferred embodiment of the present invention, the X-ray diagnostic apparatus further comprises a holding mechanism for so holding the solid state detecting portion that the solid state detecting portion is capable of independently rotating with respect to two horizontal axes thereof, at least one of the two rotations being an offset rotation with respect to a rotation axis dislocated from a central axis of the solid state detecting portion.

In a preferred embodiment of the present invention, the holding mechanism comprises: a first holding member, connected to the solid state detecting portion at one end thereof, for enabling the solid state detecting portion to rotate about a central axis thereof; and a second holding member, so connected to the other end of the first holding member at one end thereof as to be perpendicular to a longitudinal direction of the first holding member for enabling the solid state detecting portion to be offset-rotatable about a rotation axis dislocated from the central axis thereof.

In a preferred embodiment of the present invention, at least the second holding member extends and contracts along a longitudinal direction thereof.

In a preferred embodiment of the present invention, the holding mechanism comprises a direct drive motor having a bearing for holding a load and enabling each rotating control, and a clutch for electrically holding each positioning determined by each rotating control, and wherein when power is turned off, the direct drive motor performs an offlock braking operation for fixing the solid state detecting portion to a positioning at a time of power turning off.

In a preferred embodiment of the present invention, positioning of the X-ray generating portion is controlled in a position opposed to the solid state detecting portion when positioning of the solid state detecting portion is controlled.

In a preferred embodiment of the present invention, the solid state detecting portion has a clutch control switch for manually on-off controlling the clutch of the holding mechanism, and positioning of the X-ray generating portion is controlled in accordance with a position of the solid state detecting portion manually controlled in positioning.

In a preferred embodiment of the present invention, the positioning of the X-ray generating portion is controlled while a SID is constantly held.

In a preferred embodiment of the present invention, the X-ray diagnostic apparatus further comprises means for setting the SID.

In a preferred embodiment of the present invention, the X-ray diagnostic apparatus further comprises SID display means for displaying the set SID.

In a preferred embodiment of the present invention, the X-ray diagnostic apparatus further comprises mode display means for displaying an indication of positioning mode which indicates that the SID is constantly held.

In a preferred embodiment of the present invention, the X-ray generating portion comprises an arm formed in an arc shape of ¼ circle which supports an X-ray generator.

The nature, principle and utility of the invention will become more apparent from the following detailed description when read in conjunction with the accompanying drawings.

BRIEF DESCRIPTION OF THE DRAWINGS

In the accompanying drawings:

FIG. 7 is a view for explaining a case in which the separated holding devices is used in a style of over-table tube.

DESCRIPTION OF THE PREFERRED EMBODIMENTS

The preferred embodiments of an X-ray diagnostic apparatus according to the present invention will next be described in detail with reference to the accompanying drawings.

Figure 1:
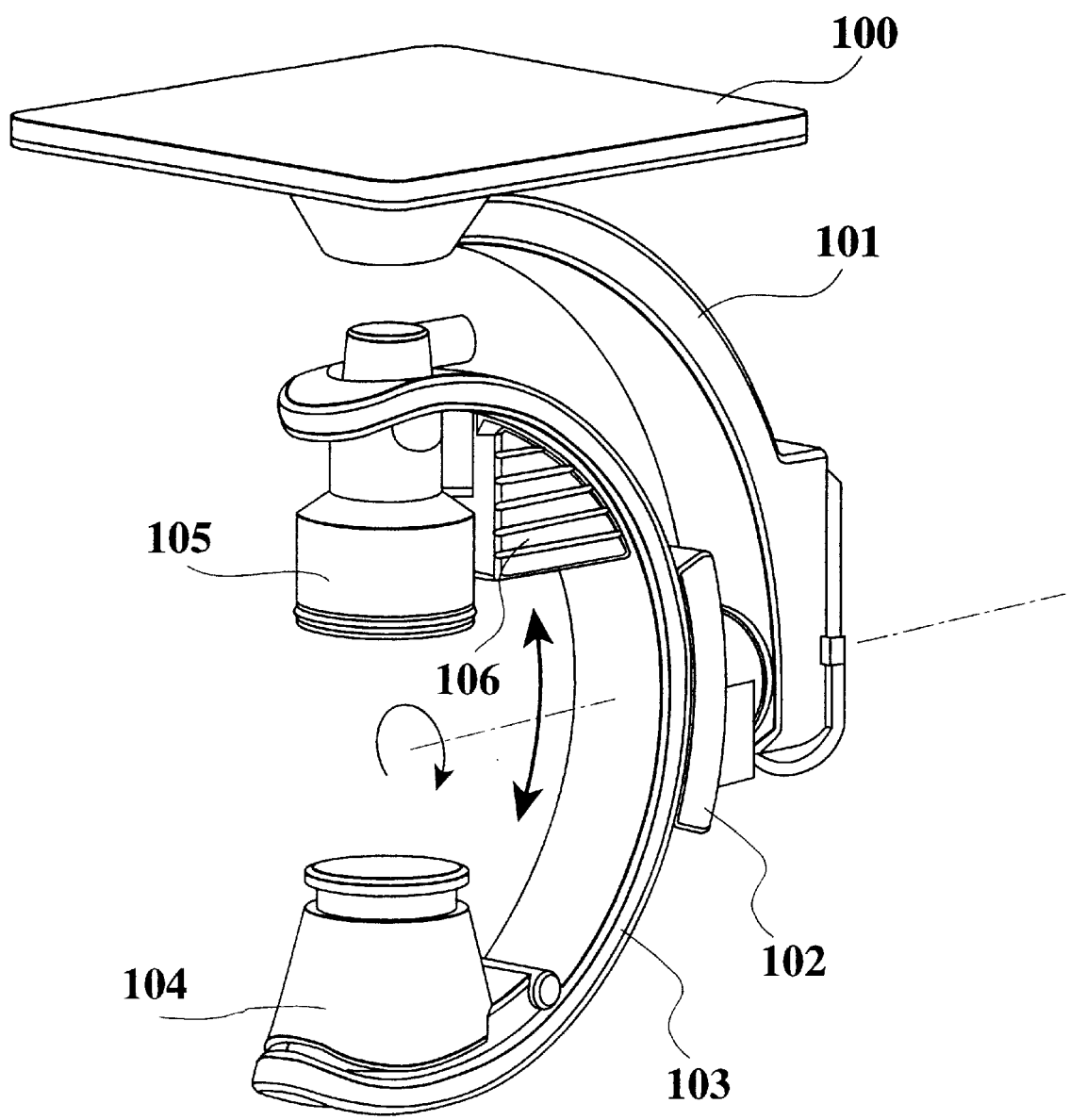
FIG. 1 is a perspective view of a holding device for a circulatory organ as one of conventional diagnostic devices.
Figure 2A:
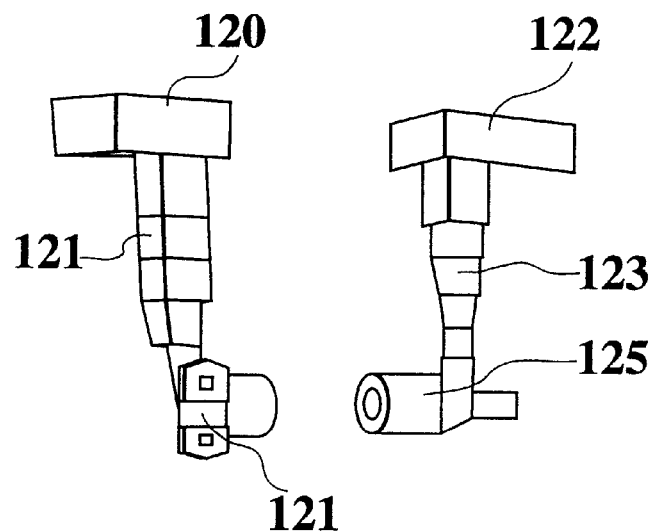
FIG. 2A is a perspective view of separated holding devices called BC arms as one of the conventional X-ray diagnostic apparatuss.
Figure 2B:
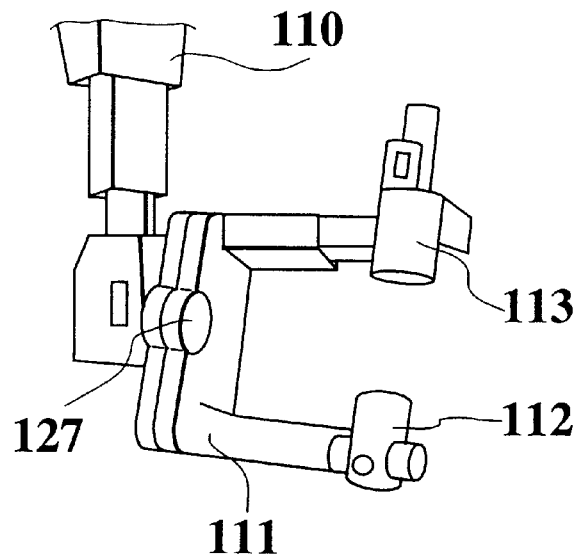
FIG. 2B is a perspective view of an U-type arm used together with the BC arms shown in FIG. 2A.
Figure 3:
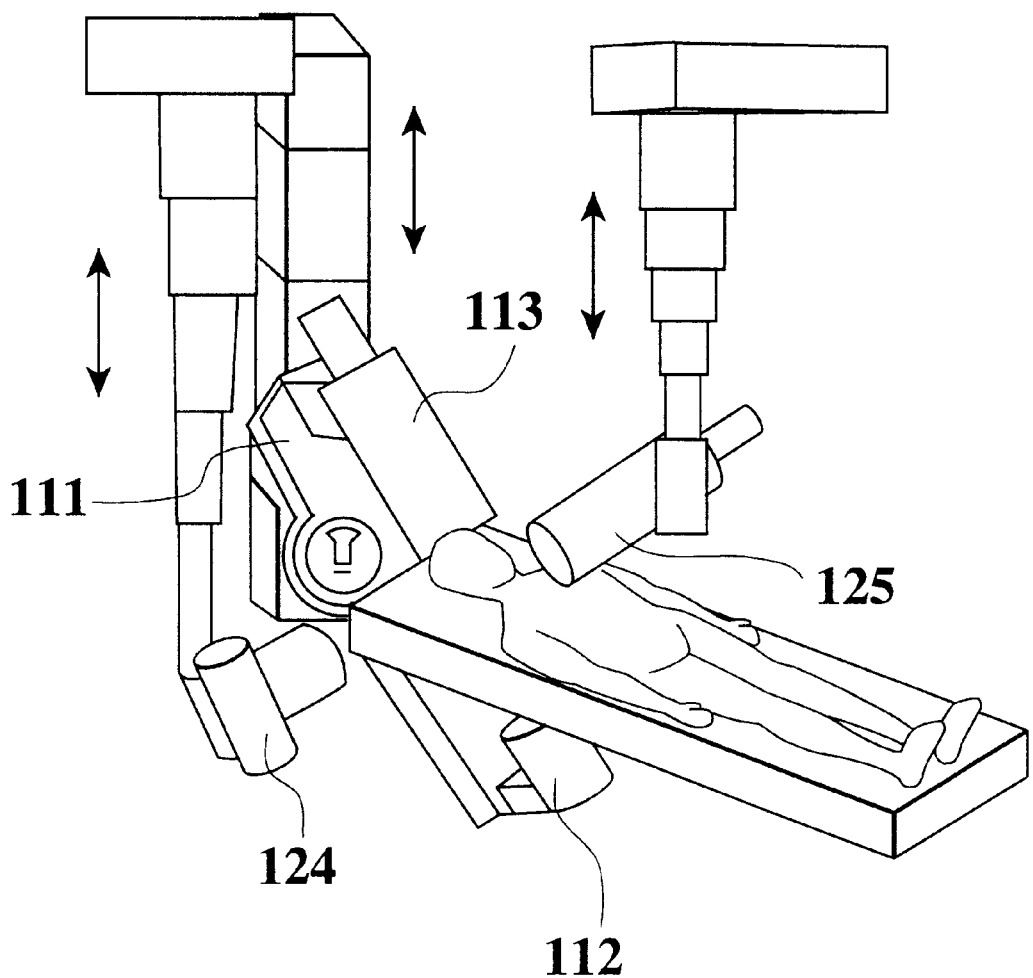
FIG. 3 is a view showing a situation in which a biplane radiography is performed by using the separated holding devices as a lateral positioner together with the U-type arm.
Figure 4:
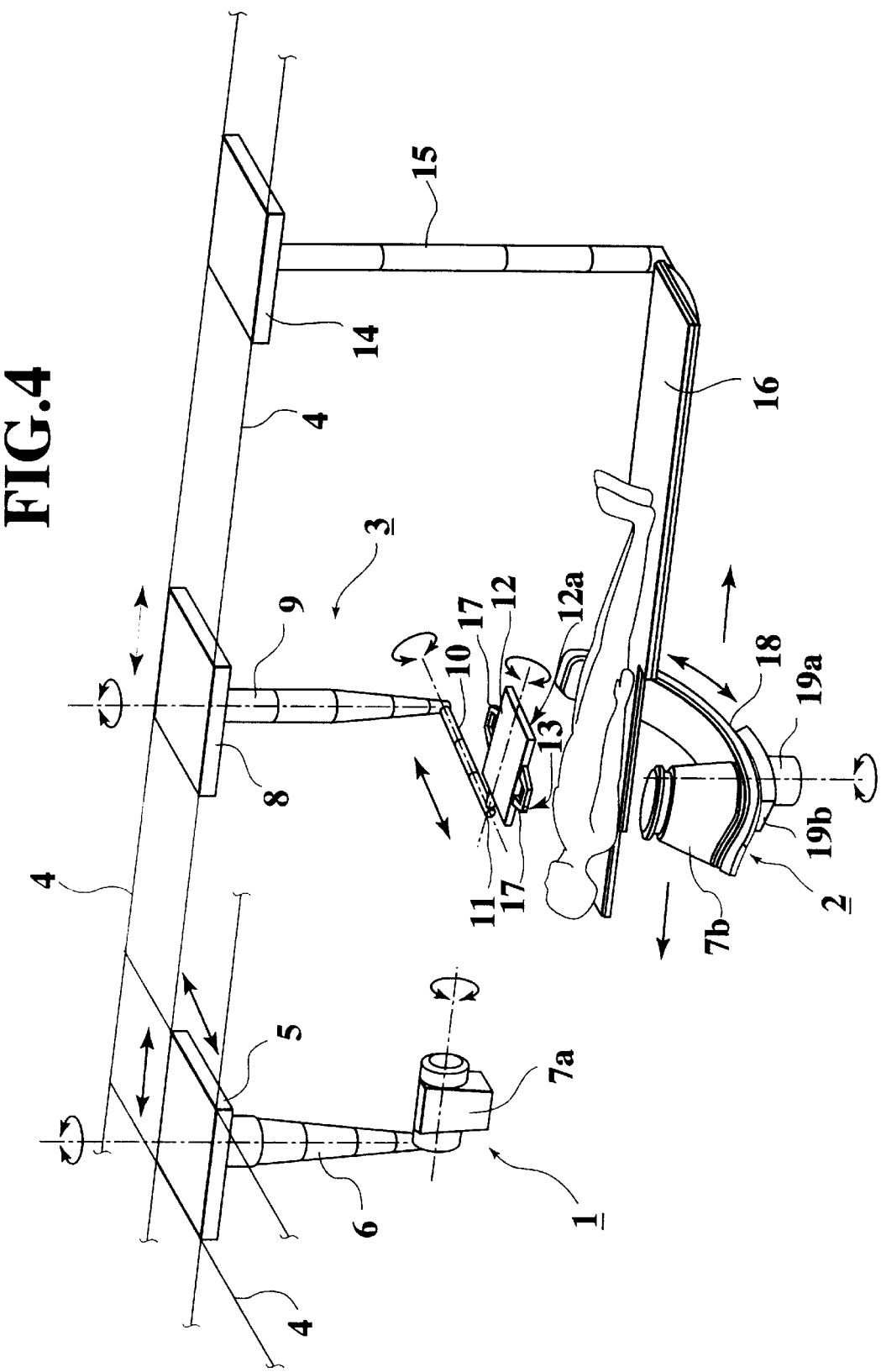
FIG. 4 is a view for explaining separated holding devices to which one embodiment of an X-ray diagnostic apparatus according to the present invention is applied.

The X-ray diagnostic apparatus according to the present invention can be applied to separated holding devices as shown in FIG. 4. This separated holding devices according to the present invention comprises a first X-ray generating portion 1 for imaging in the style of an over-table tube (the word "imaging" includes both "fluoroscopy" performed by irradiating a small amount of X-ray and "radiography" performed by irradiating a large amount of X-ray), a second X-ray generating portion 2 for imaging in the style of an under-table tube, an X-ray detecting portion 3 for taking-in X-ray information by the irradiation of X-ray from each of the X-ray generating portions 1, 2, and a diagnostic table 16 for placing a subject to be imaged thereon.

The first X-ray generating portion 1 for imaging in the style of the over-table tube comprises a stay portion 6 which elastically extends and contracts, an X-ray generator 7a arranged at one end (an end portion near a floor side) of the stay portion 6, and a ceiling base 5 connected to the other end (an end portion on a ceiling side) of the stay portion 6. The ceiling base 5 can slide along a rail 4 attached on the ceiling so that the entire first X-ray generating portion 1 can move along the rail 4.

The stay portion 6 is provided with a spring balancer arranged in the stay portion 6 so as to be mechanically compensated in gravity.

Namely, the X-ray generator 7a is held in such a state as to be suspended from the ceiling by means of the stay portion 6, thereby being able to move along the rail 4 and thus relatively move with respect to the subject placed on the diagnostic table 16.

The second X-ray generating portion 2 for imaging in the style of the under-table tube comprises a stay portion 19a fixed to the floor, a holder 19b mounted on the stay portion 19a in such a way as to be rotatable about the stay, a slide arm 18 slidably mounted on the holder 19b and having a ¼ circular shape, and an X-ray generator 7b fixed to one end of the slide arm 18. By virtue of the constitution of the second X-ray generating portion 2, the X-ray generator 7b can be positioned on any part of a lower half spherical surface under the subject(the diagnostic table 16).

The diagnostic table 16 is supported by an elastic stay portion 15 at its one end with respect to a longitudinal direction. The stay portion 15 is connected to a ceiling base 14 movable along the rail 4. Therefore, the diagnostic table 16 can move along the rail 4.

The X-ray detecting portion 3 comprises an elastic stay portion 9 connected to a ceiling base 8 movable along the rail 4, and a solid state detector 12 having a detecting face 12a on one face thereof. The detecting face 12a is formed by two dimensionally arranging plural solid state image pickup elements.

The solid state detector 12 is provided with an arm 11 for central rotation which is formed in such a way that a central shaft of the solid state detector 12 is extended. An elastic arm 10 for offset rotation is connected to an end portion of the arm 11 for central rotation, the end portion which is other than one connected to the solid state detector 12. The arm 10 for offset rotation is perpendicular to the arm 11 for central rotation. An end portion of the arm 10 for offset rotation, the end portion which is other than one connected to the arm 11 for central rotation, is connected to the stay portion 9.

By virtue of such a constitution, the X-ray detecting portion 3 can move along the rail 4. Further, the arm 11 for central rotation enables central rotation about the central axis of the solid state detector 12, and the arm 10 for offset rotation enables offset rotation having an offset with respect to the central rotation. Since the arm 10 for offset rotation is extensible and contractible, the solid state detector 12 can be set to various positions in upward, downward, leftward, rightward and slanting directions of the subject placed on the diagnostic table 16.

Here, only the arm 10 for offset rotation is set to be extensible and contractible, but the arm 11 for central rotation may be also set to be extensible and contractible. In this case, a degree of freedom of positioning of the solid state detector 12 can be further increased.

The solid state detector 12 is provided with handles at its both side portions with respect to the longitudinal direction. An operator grips the handles 17 to manually set positioning of the solid state detector 12. Each of the handles 17 has a clutch control switch 13 at its position where a right hand thumb may turn on and off the switch 13 when the operator grips the handle 17 by the right hand, for example.

The clutch control switch 13 is used to control connection and disconnection of a clutch for fixing the X-ray detecting portion 3 in a position to be set. The clutch of each movable portion is disconnected by turning on the clutch control switch 13 so that positioning control can be manually performed. The clutch of each movable portion is connected by turning off the clutch control switch 13 so that the X-ray detecting portion 3 is fixed in the position at the time when the switch 13 is turned off.

Figure 5:
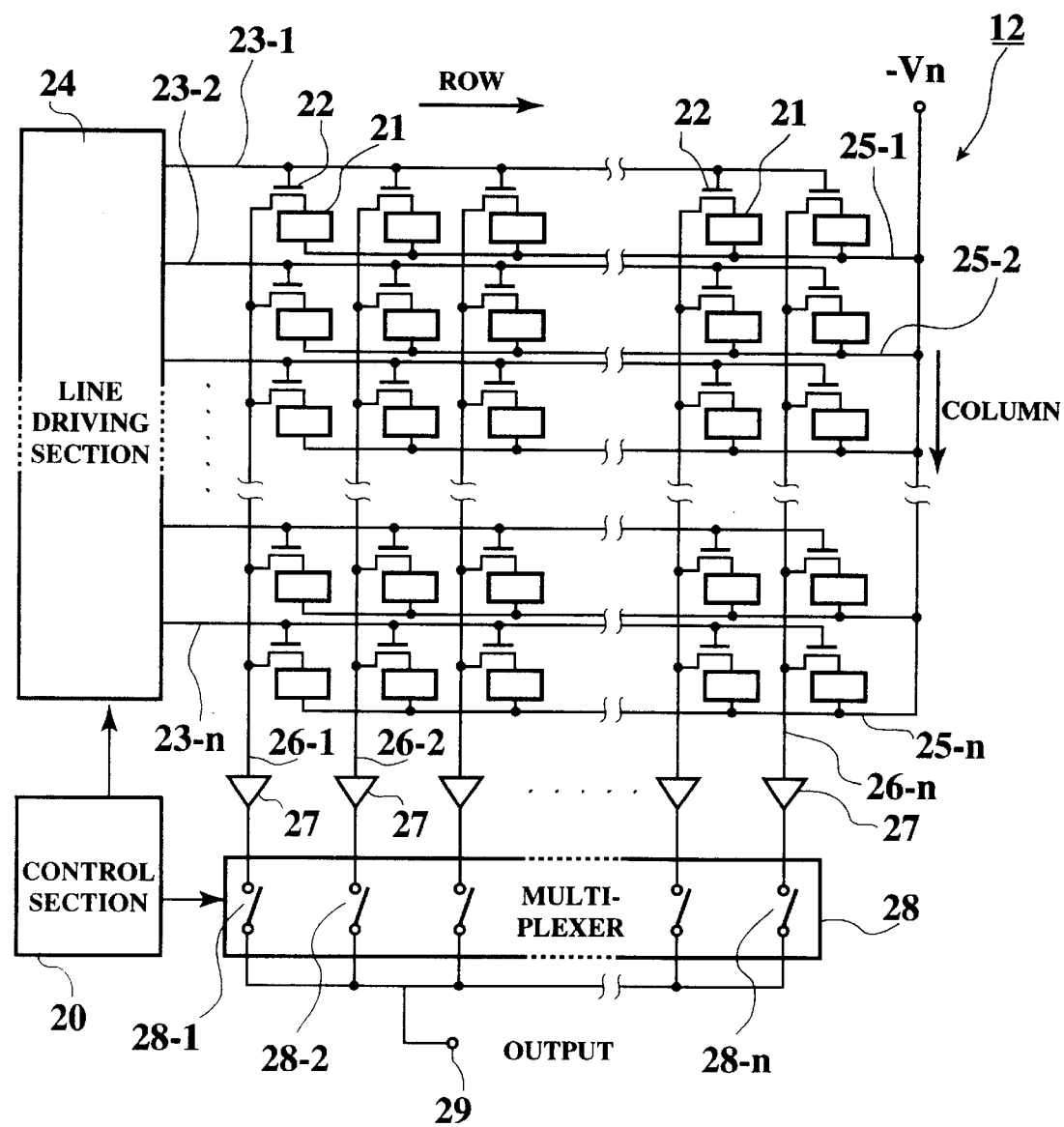
FIG. 5 is a view showing the constitution of a solid state detector arranged in the separated holding devices shown in FIG. 4.

Here, for example, as shown in FIG. 5, the solid state detector 12 is made by two-dimensionally arraying X-ray detecting elements in column and row directions. Each of the X-ray detecting elements comproses a pixel 21 and a thin film transistor (TFT) 22. The pixel 21 senses a visible ray converted from X-ray information by a phosphor (a phosphor 35 in FIG. 6) which will be explained later, and forms an electric charge corresponding to an incident light amount of the visible ray. The thin film transistor 22 is used as a switch for reading the electric charge accumulated in the pixel 21.

Each pixel 21 has a photodiode for sensing the visible ray and forming the electric charge corresponding to the incident light amount, and a capacitor (a capacitor for accumulation) for accumulating the electric charge formed by this photodiode.

A connection point of a cathode terminal of the photodiode and one terminal of the capacitor for accumulation is connected to a backward bias power source (−Vn) through power lines 25-1, 25-2, . . . , 25-n. A connection point of an anode terminal of the photodiode and the other terminal of the capacitor for accumulation is connected to a source terminal of each TFT 22.

Gate terminals of the TFTs 22 in each row are commonly connected to each other through respective reading-out lines 23-1, 23-2, . . . , 23-n, and are connected to respective line output terminals of a line driving section 24.

Drain terminals of the TFTs 22 in each column are commonly connected to each other through respective vertical transfer lines 26-1, 26-2, . . . , 26-n, and are connected to respective switches 28-1, 28-2, . . . , 28-n of a multiplexer 28 through a respective reading-out amplifier 27.

Upon reading, a control section 20 sequentially performs turning-on control of the TFTs 22 of the respective reading-out lines 23-1, 23-2, . . . , 23-n through the line driving section 24 to sequentially select and control the accumulated electric charges on the respective reading-out lines 23-1, 23-2, . . . , 23-n. Then the control section 20 performs on/off control of the respective switches 28-1, 28-2, . . . , 28-n of the multiplexer 28 so as to sequentially select the accumulated electric charges in each line supplied to the multiplexer 28. Accordingly, a fluoroscopic image signal or a radiographic image signal can be outputted through an output terminal 29.

Figure 6:
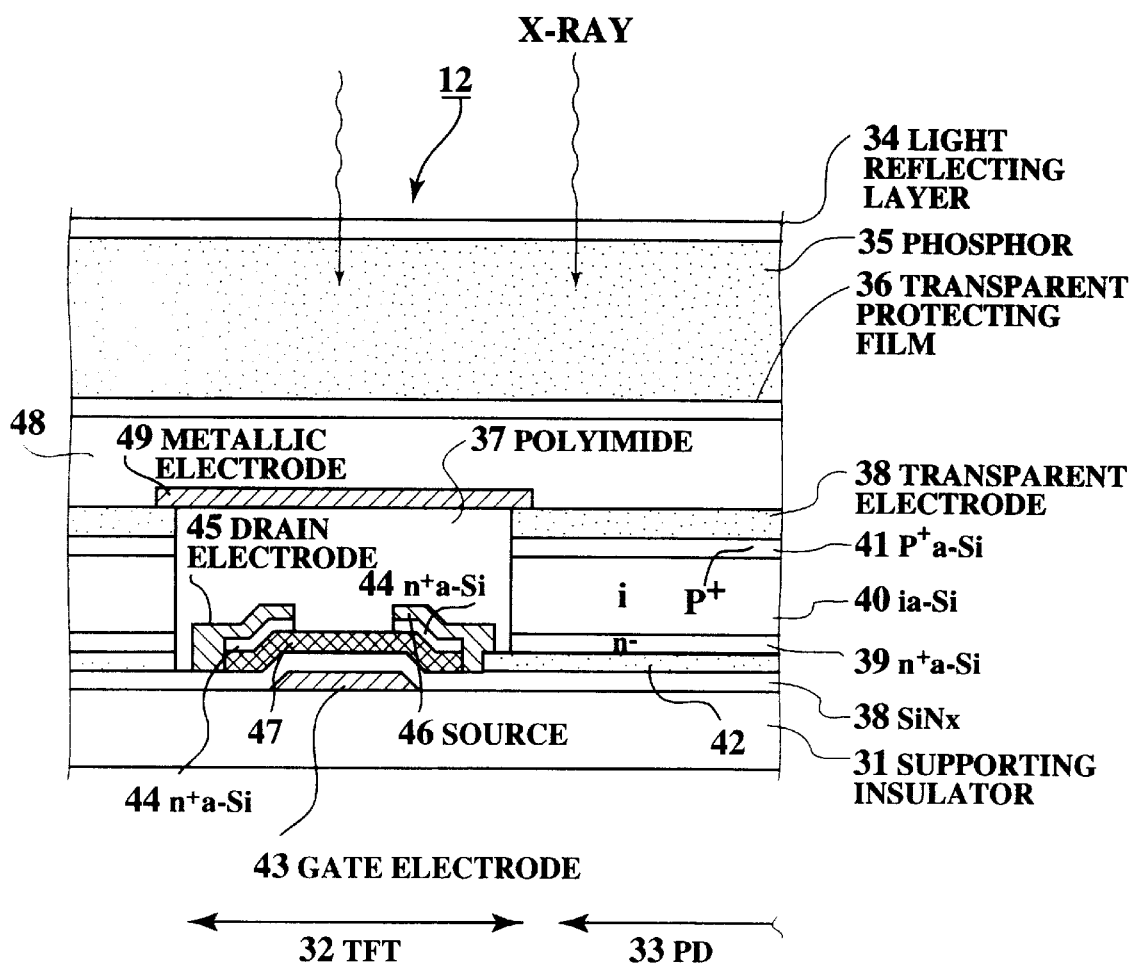
FIG. 6 is a cross sectional view of the solid state detector.

Further specifically, a cross section of each X-ray detecting element is formed as shown in FIG. 6. The TFT 22 is formed on a TFT area 32 on a supporting insulator 31 and the pixel 21 is formed on a pixel area 33 (PD area) on the supporting insulator 31.

In the TFT area 32, a gate electrode 43 is formed on the supporting insulator 31 and an SiNx layer 38 is laminated on the gate electrode 43. An n-Si layer 47 is laminated on the SiNx layer 38. A drain electrode 45 is formed on the n-Si layer 47 through an $n^+$ a-Si layer 44 and a source electrode 46 is formed on the n-Si layer 47 through the $n^+$ a-Si layer 44. A first polyimide resin layer 37 is laminated on the TFT area 32 and a metallic electrode 49 is formed on the first polyimide resin layer 37.

In the PD area 33, an SiNx layer 38 and a transparent electrode 42 connected to the source electrode 46 are laminated on the supporting insulator 31. An $n^+$ a-Si layer 39, an i a-Si layer 40, a $p^+$ a-Si layer 41 and a transparent electrode 38 are laminated in that order on the transparent electrode 42 so that a photodiode of a Pin structure is formed.

Next, a second polyimide resin layer 48 is laminated on the TFT area 32 and the PD area 33. A transparent protecting film 36 is laminated on the second polyimide resin layer 48. A phosphor 35 for converting the above X-ray information to a visible ray is formed on the transparent protecting film 36. A light reflecting layer 34 for reflecting the visible ray and taking only the X-ray information in is formed on the phosphor 35.

In the solid state detector 12 having such a constitution, when the X-ray information formed by irradiating an X-ray to a subject is inputted to the solid state detector 12, a visible ray is reflected on the light reflecting layer 34 and only the X-ray information is inputted to the phosphor 35 through the light reflecting layer 34 and is converted to a visible ray corresponding to the X-ray information. The visible ray is transmitted through the transparent protecting film 36 and the second polyimide resin layer 48 and is further received by a photodiode sensitive to the visible ray through the transparent electrode 38.

The photodiode forms an electric charge corresponding to the visible ray and supplies the electric charge to the capacitor for accumulation. Thus, the electric charge (an imaging signal) corresponding to the X-ray information is accumulated into the capacitor for accumulation. The electric charge accumulated into the capacitor for accumulation is read by reading-out control of the control section 20 as mentioned above through reading-out lines 23-1, 23-2, . . . , 23-n line byu line and is supplied to a monitor device, etc. through the multiplexer 18 and the output terminal 29.

In the meanwhile, when such separated holding devices are used in the style of an under-table tube, a subject is placed on the diagnostic table 16 as shown in FIG. 4 and the X-ray detecting portion 3 is controlled and moved to be able to acquire X-ray information with respect to a desirable portion of the subject.

The movement of the X-ray detecting portion 3 is performed by controlling the rotation of a roller provided on the ceiling base 8 by a motor and a transmission system. Thus, the X-ray detecting portion 3 can move along the rail 4.

A stay portion 9 is rotatably attached to the ceiling base 8 through a bearing, etc. so that the solid state detector 12 can be rotatable about a vertical axis. The solid state detector 12 is rotated by transmitting power of a motor by a chain sprocket, etc.

Further, for example, the stay portion 9 can be vertically freely extended and contracted by a divisional structure such as a bellows mechanism or a fishing rod. A controlled stroke position of the stay portion 9 is held by a spring balancer, etc. installed therein.

A movement of the offset rotating arm 10 attached to the stay portion 9 is controlled by a driving system to move the solid state detector 12 in a horizontal transversal direction (an extending direction of the offset rotating arm 10).

The solid state detector 12 can be centrally rotated by means of the central rotating arm 11 arranged along a central axis thereof and can be offset-rotated by means of the offset rotating arm 10.

For example, these rotations are performed by a direct drive motor (D.D motor) having a load supporting bearing. Unbalance torque of the D.D motor caused by the offset rotation is caused since a center of gravity of the solid state detector 12 is dislocated from its center of rotation (the offset rotating arm 10) by the offset rotation of the solid state detector 12. This unbalance torque can be univocally calculated irrespective of a rotating position by the central rotation if a rotating position of the solid state detector 12 by the offset rotation is determined. Therefore, an operation of the D.D motor is controlled in accordance with the rotating position of the solid state detector 12 so as to cancel the unbalance torque. Thus, the rotating balance of the solid state detector 12 can be kept.

When the solid state detector 12 is electrically balanced in this way, there is a fear that a brake is turned off when power supplied to the D.D motor is turned off. Therefore, the D.D motor is provided with an offlock brake for holding the rotating position of the solid state detector 12 when the power is turned off. Thus, the rotating position of the solid state detector 12 is held even when the power is turned off. Therefore, it is possible to prevent the disadvantages that the brake is turned off.

The D.D motor which can be directly connected to a load is used so that no power transmission system is required and highly accurate positioning can be performed.

The central axis of the central rotation and the central axis of the offset rotation are perpendicular to each other (an offset is provided). Therefore, solid state detector 12 does not interfere (contact) with each of the arms 10, 11 on each rotation so that the solid state detector 12 can be rotated through 360° in each rotation.

The central rotating arm 11 is arranged along the central axis of the solid state detector 12 (there is no offset) so that the rotating balance can be kept and the size of a power system can be reduced.

Thus, the solid state detector 12 is electrically compensated in gravity by the D.D motor having the offlock brake, etc.

Here, positioning of the solid state detector 12 can be also adjusted by a manual operation. In such manual control, the solid state detector 12 has two modes and these two modes are switched at an operator's will. Supposing that these two modes are an A-mode and a B-mode, the solid state detector is positioned at the operator's will in the A-mode. Namely, the solid state detector 12 can be positioned to an intended position at high speed on the basis of a sense of the operator without any restriction in positioning path.

Specifically, the solid state detector 12 is provided with handles 17 which the operator grips to turn on the clutch control switch 13. When the clutch control switch 13 is turned on, a clutch of each movable portion is disconnected and positioning of the solid state detector can be manually controlled.

The rotating shafts of the offset rotating arm 10 and the central rotating arm 11 is provided with a force detecting device made by a distortion gauge, etc. Unbalances caused by gravity and external force are discriminated from each other by this force detecting device. When the operator applies operating force to the solid state detector 12 by the manual operation, the solid state detector 12 can be rotated in accordance with this operating force while connecting to a power source. Thus, the solid state detector 12 can be controlled to move to a desirable position of the operator.

The operator manually controls the solid state detector 12 to move to a desirable position and then turns off the clutch control switch 13. Thus, the clutch of each movable portion is connected and the X-ray detecting portion 3 is fixed in the position at the time when the clutch control switch 13 is turned off.

In contrast to this, in the B-mode, each angle setting operation (CRA/CAU, RAO/LAO) is performed while a SID (Source-Image Distance) is constantly held. This SID is inputted by the operator through an input portion such as a ten key arranged in a console, etc. For example, when the SID is set to 100 cm, it is impossible to move the solid state detector 12 in a position other than a position of 100 cm SID. Namely, the solid state detector 12 can be moved only on a spherical surface with an isocenter as a center. Accordingly, the solid state detector 12 is manually operated while the SID is constantly held.

When the clutch control switch 13 is turned on in this B-mode, combinations of parameters of angles and positions of movable portions in which the SID is not changed are calculated (or calculated in advance). An operation of each driving motor is controlled such that the solid state detector 12 do not move to a position other than a position determined by this combination, i.e., other than a position in which the SID is not changed.

The A-mode and B-mode are switched by a switch on the console, etc. Further, the present mode and the SID are displayed on a monitor, an indicator, etc. in addition to on the console.

When the moving control of the solid state detector 12 is switched from the manual control to automatic control, the solid state detector 12 can be operated while the SID at a manual control time is held.

Each movable portion of the solid state detector 12 is provided with a position detecting sensor such as a potentiometer, etc. When the movement of the solid state detector 12 is controlled automatically or manually in this way, the second X-ray generating portion 2 for imaging of under-table tube is automatically arranged oppositely to the detecting face 12a of the controlled and moved solid state detector 12.

Specifically, when the solid state detector 12 is manually moved, for example, a position and a direction of the solid state detector 12 are momentarily detected by the position detecting sensor such as a potentiometer, etc. six-dimensionally (positions in a three dimensional coordinate space and rotating angles with respect to these axes). A data processor momentarily calculates coordinates in a position for moving the X-ray generator 7b on the basis of these detected data. Rotation of the holder 19b as a movable portion and slide of the slide arm 18 as a movable portion are electrically controlled on the basis of the calculated position coordinate data so that the X-ray generator 7b is positioned. A motor as an electric motor and a chain belt as power transmission are utilized as concrete driving members.

As mentioned above, the slide arm 18 has a ¼ circular shape. Therefore, a range capable of irradiating an X-ray of the second X-ray generating portion 2 is set to a range on a lower half spherical surface under the subject so that an image of the subject can be picked up in the style of under-table tube.

On the other hand, when such separated holding devices are used in the style of over-table tube, the subject is placed on the diagnostic table 16 as shown in FIG. 7 and the solid state detector 12 is located at a rear side (a back side of the subject in the case of FIG. 7) of the diagnostic table 16 by controlling to extend the stay portion 9. Then, the operation of the solid state detector 12 is manually or automatically controlled to move in a position where X-ray information with respect to a desirable portion of the subject by using the above offset and central rotations.

Since the stay portion 9 can be freely extended and contracted, the solid state detector 12 can be simply located at the rear side of the diagnostic table 16. As mentioned above, since the solid state detector 12 can be independently rotated through 360° in each of the offset rotation and the central rotation, the solid state detector 12 can be set to various positionings.

When positioning of the solid state detector 12 is controlled in this way, the rotation of a roller installed in the ceiling base 5 of the first X-ray generating portion 1 as an X-ray generating portion for imaging of over-table tube is controlled by a transmission system such as a motor, a chain sprocket, etc. so that the X-ray generator 7a is automatically located oppositely to the detecting face 12a of the solid state detector 12 controlled in positioning. Thus, an image of the subject can be picked up in the style of over-table tube.

As can be clearly seen from the above explanation, the first X-ray generating portion 1 for imaging of over-table tube, the second X-ray generating portion 2 for imaging of under-table tube, and the X-ray detecting portion 3 having the solid state detector 12 formed by plural solid state detecting elements can be independently moved in the separated holding devices in the embodiment. The solid state detector 12 can be centrally rotated through 360° about a central axis of the solid state detector 12 and can be offset-rotated through 360° in a state in which an offset is provided in this central rotation.

Therefore, it is possible to rapidly and accurately provide the over-table tube typed imaging and the under-table tube typed imaging applicable to various positionings so that it can be widely applied to clinical fields.

Positioning of the solid state detector 12 can be also manually controlled so that fine positioning control can be performed in accordance with an operator's will. Accordingly, a burden of the operator caused by a complicated operation using an electric movement can be reduced.

Further, since the first X-ray generating portion 1, the second X-ray generating portion 2 and the X-ray detecting portion 3 are independently provided, no C-arm, etc. for oppositely holding the X-ray detecting portion and the X-ray generating portion are required so that a mechanical interference can be avoided and further a working space can be secured and a field of view can be enlarged.

In the case of a patient carried by an ambulance car, for example, no diseased portion is known in many cases since the patient loses consciousness, etc. In such cases, at first it is necessary to specify causes by performing fluoroscopy and radiography and make a medical plan. However, if it takes long time to perform the fluoroscopy and the radiography, this time endangers life. The separated holding devices in the present invention can rapidly and accurately perform the fluoroscopy and the radiography in various positionings as mentioned above. Therefore, the separated holding devices can instantly perform the fluoroscopy and the radiography in precise positioning using a manual operation, etc. by only moving the patient carried by the ambulance car to an inspecting room in a state in which the patient is placed on a stretcher. Therefore, a subsequent medical plan can be instantly made and the separated holding devices can greatly contribute to lifesaving.

In the above explanation in the embodiment, the detecting face 12a of the solid state detector 12 is arranged only on one side, but may be arranged on both sides of the solid state detector 12. In this case, time and labor for rotating the detecting face of the solid state detector 12 can be omitted both when the fluoroscopy and the radiography are changed in style from the over-table tube to the under-table tube, and when the fluoroscopy and the radiography is changed in style from the under-table tube to the over-table tube. Accordingly, the separated holding devices can greatly contribute to the above mentioned rapid fluoroscopy and radiography.

As mentioned above, in accordance with the X-ray diagnostic apparatus in the present invention, various positionings can be performed accurately and rapidly so that it is possible to accommodate to various ranges of application.

It should be understood that many modifications and adaptations of the invention will become apparent to those skilled in the art and it is intended to encompass such obvious modifications and changes in the scope of the claims appended hereto.

What is claimed is:

1. An X-ray diagnostic apparatus comprising:
   an X-ray generating portion configured to irradiate an X-ray to a subject;
   a solid state detecting portion formed by plural solid state detecting elements and configured to detect the X-ray irradiated from the X-ray generating portion and movably provided independently of the X-ray generating portion; and
   a holding mechanism configured to hold the solid state detecting portion such that the solid state detecting portion is horizontally movable, pivotable on a vertical axis, pivotable on a horizontal axis which crosses the vertical axis and rotatable about an axis which crosses the horizontal axis and is parallel to a detecting plane of the solid state detecting portion,
   wherein the X-ray generating portion comprises at least one of an X-ray generating portion for an under-table tube capable of imaging in a style of under-table tube and an X-ray generating portion for an over-table tube capable of imaging in a style of over-table tube.

2. The X-ray diagnostic apparatus as claimed in claim 1, wherein the holding mechanism comprises:
   a sliding base configured to slide along a ceiling;
   a stay having one end rotatably connected to the sliding base;
   a first arm having one end rotatably connected to the other end of the stay, the first arm being perpendicular to the stay; and
   a second arm having one end rotatable connected to the other end of the first arm, the second arm being perpendicular to the first arm, and having the other end connected to a side of the solid state detecting portion.

3. The X-ray diagnostic apparatus as claimed in claim 2, wherein the stay and the first arm are configured to be extendible and contractible along longitudinal directions thereof, respectively.

4. The X-ray diagnostic apparatus as claimed in claim 2, wherein the holding mechanism further comprises:
   a direct drive motor having a bearing configured to hold a load and enabling each rotating control; and
   a clutch configured to electrically hold each positioning determined by each rotating control, and wherein
   when power is turned off, the direct drive motor performs an offlock braking operation for fixing the solid state detecting portion to a positioning at a time of power turning off.

5. The X-ray diagnostic apparatus as claimed in claim 4, wherein positioning of the X-ray generating portion is controlled in a position opposed to the solid state detecting portion when positioning of the solid state detecting portion is controlled.

6. The X-ray diagnostic apparatus as claimed in claim 5, wherein the solid state detecting portion has a clutch control switch configured to manually on-off control the clutch of the holding mechanism, and positioning of the X-ray generating portion is controlled in accordance with a position of the solid state detecting portion manually controlled in positioning.

7. The X-ray diagnostic apparatus as claimed in claim 6, wherein the positioning of the X-ray generating portion is controlled while a SID is constantly held.

8. The X-ray diagnostic apparatus as claimed in claim 7, further comprising a mode display mechanism configured to display an indication of positioning mode which indicates that the SID is constantly held.

9. An X-ray diagnostic apparatus comprising:
   an X-ray generating portion configured to irradiate an X-ray to a subject;
   a solid state detecting portion formed by plural solid state detecting elements and configured to detect the X-ray irradiated from the X-ray generating portion and movably provided independently of the X-ray generating portion;
   a sliding base configured to slide along a ceiling;
   a stay having one end rotatably connected to the sliding base;
   a first arm having one end rotatably connected to the other end of the stay, the first arm being perpendicular to the stay; and
   a second arm having one end rotatably connected to the other end of the first arm, the second arm being perpendicular to the first arm, and having the other end connected to a side of the solid state detecting portion.

10. The X-ray diagnostic apparatus as claimed in claim 9, wherein the stay and the first arm are configured to be extendable and contractable along longitudinal directions thereof, respectively.

11. The X-ray diagnostic apparatus as claimed in claim 9, wherein the holding mechanism comprises a direct drive motor having a bearing configured to hold a load and enabling each rotating control, and
   a clutch configured to electrically hold each positioning determined by each rotating control, and wherein
   when power is turned off, the direct drive motor performs an offlock braking operation for fixing the solid state detecting portion to a positioning at a time of power turning off.

12. The X-ray diagnostic apparatus as claimed in claim 11, wherein positioning of the X-ray generating portion is controlled in a position opposed to the solid state detecting portion when positioning of the solid state detecting portion is controlled.

13. The X-ray diagnostic apparatus as claimed in claim 12, wherein the solid state detecting portion has a clutch control switch for manually on-off controlling the clutch of the holding mechanism, and positioning of the X-ray generating portion is controlled in accordance with a position of the solid state detecting portion manually controlled in positioning.

14. The X-ray diagnostic apparatus as claimed in claim 13, wherein the positioning of the X-ray generating portion is controlled while a SID is constantly held.

15. The X-ray diagnostic apparatus as claimed in claim 14, wherein the X-ray diagnostic apparatus further comprises means for setting the SID.

16. The X-ray diagnostic apparatus as claimed in claim 15, wherein the X-ray diagnostic apparatus further comprises SID display means for displaying the set SID.

17. The X-ray diagnostic apparatus as claimed in claim 14, wherein the X-ray diagnostic apparatus further comprises mode display means for displaying an indication of positioning mode which indicates that the SID is constantly held.

18. An X-ray diagnostic apparatus comprising:
   an X-ray generating portion configured to irradiate an X-ray to a subject;
   a solid state detecting portion formed by plural solid state detecting elements and configured to detect the X-ray irradiated from the X-ray generating portion and movably provided independently of the X-ray generating portion; and
   a holding mechanism configured to hold the solid state detecting portion such that the solid state detecting portion is horizontally movable, pivotable on a vertical axis, pivotable on a horizontal axis which crosses the vertical axis and rotatable about an axis which crosses the horizontal axis and is parallel to a detecting plane of the solid state detecting portion,
   wherein positioning of the X-ray generating portion is controlled in a position opposed to the solid state detecting portion when positioning of the solid state detecting portion is controlled.

19. The X-ray diagnostic apparatus as claimed in claim 18, wherein the X-ray generating portion comprises an arm formed in an arc shape of ¼ circle which supports an X-ray generator.

20. The X-ray diagnostic apparatus as claimed in claim 18, wherein the holding mechanism comprises:
   a sliding base configured to slide along a ceiling;
   a stay having one end rotatably connected to the sliding base;
   a first arm having one end rotatably connected to the other end of the stay, the first arm being perpendicular to the stay; and
   a second arm having one end rotatably connected to the other end of the first arm, the second arm being perpendicular to the first arm, and having the other end connected to a side of the solid state detecting portion.

21. The X-ray diagnostic, apparatus as claimed in claim 20, wherein the stay and the first arm are configured to be extendible and contractible along longitudinal directions thereof, respectively.

22. The X-ray diagnostic apparatus as claimed in claim 20, wherein the holding mechanism further comprises:
   a direct drive motor having a bearing configured to hold a load and enabling each rotating control; and
   a clutch configured to electrically hold each positioning determined by each rotating control, and wherein
   when power is turned off, the direct drive motor performs an offlock braking operation for fixing the solid state detecting portion to a positioning at a time of power turning off.

23. The X-ray diagnostic apparatus as claimed in claim 22, wherein the solid state detecting portion has a clutch control switch configured to manually on-off control the clutch of the holding mechanism, and positioning of the X-ray generating portion is controlled in accordance with a position of the solid state detecting portion manually controlled in positioning.

24. The X-ray diagnostic apparatus as claimed in claim 23, wherein the positioning of the X-ray generating portion is controlled while a SID is constantly held.

25. The X-ray diagnostic apparatus as claimed in claim 24, further comprising a setting mechanism configured to set the SID.

26. The X-ray diagnostic apparatus as claimed in claim 24, further comprising a mode display mechanism configured to display an indication of positioning mode which indicates that the SID is constantly held.

* * * * *